US00PP09599P

United States Patent [19]

Skotak, Jr.

[11] Patent Number: Plant 9,599

[45] Date of Patent: Jul. 2, 1996

[54] NEOREGELIA PLANT NAMED 'MORADO'

[75] Inventor: Chester Skotak, Jr., Alajuela, Costa Rica

[73] Assignee: Dura Flor S.A., Alajuela, Costa Rica

[21] Appl. No.: 422,583

[22] Filed: Apr. 14, 1995

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new and distinct cultivar of *Neoregelia* named 'Morado,' characterized by leaves that have a creamy white margin (RHS 159B) and dark green center (RHS 136B) with slight variegation at the edges of the green center; innermost leaves at the center of the rosette that are overlayed with a purple color and plants hold this purple color for approximately 4 to 6 months during and after flowering; and abundant production of offsets.

3 Drawing Sheets

The present invention comprises a new and distinctive cultivar of Neoregelia hybrid, hereinafter referred to by the cultivar name 'Morado.' Neoregelia species are tank epiphytes with stemless inflorescences and flowers that barely rise above the water in the centers of plants. 'Morado' can be advantageously grown as a single pot plant in order to display its symmetrical rosette plant habit and colorful foliage.

The new cultivar is a product of a planned breeding program, and was originated from a cross made during such a program in Balsa, Costa Rica in 1988. The female, or seed parent was *Neoregelia carolinae lineata*×*Neoregelia princeps.* The male, or pollen parent, was *Neoregelia concentrioa.*

'Morado' was discovered and selected as a flowering plant within the progeny of the stated cross by Chester Skotak, Jr. in 1990 in a controlled environment in a nursery in Balsa, Costa Rica. Subsequent asexual reproduction by removal of offsets has demonstrated that the combination of characteristics as herein disclosed for the new cultivar are firmly fixed and are retained through successive generations of asexual reproduction.

The new cultivar has not been observed under all possible environmental conditions. The phenotype may vary with variations in environment such as temperature, light intensity, and day length, without any variation in the genotype of the plant.

The following traits have been repeatedly observed and are determined to be basic characteristics of 'Morado' that in combination distinguish this Neoregelia as a new and distinct cultivar:

1. Leaves have a creamy white margin (RHS 159B) and dark green center (RHS 136B) with slight variegation at edges of the green center.
2. The innermost leaves at the center of the rosette are overlayed with purple (Exotica).
3. The innermost leaves at the center of the rosette hold their purple color for four to six months during and after flowering.
4. The plant produces large numbers of offsets.

The following observations, measurements and values describe plants grown in Balsa, Costa Rica and Goulds, Fla., USA, under greenhouse conditions which closely approximate those generally used in horticultural practice. Color references are made to The Royal Horticultural Society (RHS) Colour Chart and the color chart from Graf, Alfred Byrd, Exotica Series 3, 6th Edition, Roehrs Co., Inc., East Rutherford, N.J. (1973), except where general color terms of ordinary significance are used. The RHS color values were determined at approximately 12 p.m. on Apr. 12, 1995 in Washington, D.C., USA from photographs of plants grown in Goulds, Fla., USA.

The new cultivar can be compared to *Neoregelia concentrica.* 'Morado' has wide leaves like *N. concentrica* but 'Morado' has a plant habit that is much smaller and compact than *N. concentrica.*

The accompanying photographic drawings show typical characteristics of the new cultivar, with colors being as true as possible with illustrations of this type. The purple color at the base of the innermost leaves is not accurately shown on these photographs.

Sheet 1 is a side view of the plant.

Sheet 2 is a top view of the plant.

Sheet 3 is a closeup of the center of the plant.

Classification:

*Botanical.*—Neoregalia hybrid, cv. 'Morado'.

*Commercial.*—Neoregelia 'Morado'.

Parentage:

*Male Parent.*—*Neoregelia concentrica.*

*Female Parent.*—*Neoregelia carolinae lineata*×*Neoregelia princeps.*

Propagation: Vegetative by removal of offsets.

Plant description: From 22 cm. to 24 cm. tall when grown in 12.5 cm pots, and approximately 45 cm. in diameter when fully grown.

*Growth habit.*—Spreading rosette.

Leaves:

*Form.*—Blades lingulate, recurved, broadly rounded and apiculate.

*Size.*—Length: 16 to 20 cm. Width: 3 cm. at tip–6 cm. at middle.

*Texture.*—Smooth.

*Veins or ribs.*—None.

*Color.*—(RHS): Upper surface: Creamy white margin (RHS 159B) and dark green center (RHS 136B) with slight variegation at edges. The innermost leaves are overlayed with purple (Exotica) and hold their color for approximately 4 to 6 months at the time of flowering.

*Lower surface.*—Same as upper surface.

*Number of leaves.*—Average 20.

Flowers:

*Arrangement.*—Deeply sunken rosette — simple and many-flowered.

*Color.*—Petal apex blue-purple (RHS 97B) with white base.

*Fruit.*—Wide, ovary ellipsoid and approximately 10 mm. long.

*Duration of flowers.*—Individually for one day but as a whole 3 to 4 weeks.

*Other significant characteristics.*—The center of the rosette of leaves maintains its purple color for 4 to 6 months.

Reproductive organs:

*Stamens.*—Pale yellow.

*Pistils.*—White. Ovary: Ellipsoid and approximately 10 mm long and 6 mm diameter.

Resistance to disease: Good resistance to fungi and insects exhibited in Costa Rica.

General observations: 'Morado' produces large numbers of offsets. Individual plants may produce up to 30 offsets per mature plant.

I claim:

1. A new and distinct cultivar of Neoregelia plant named 'Morado,' as illustrated and described.

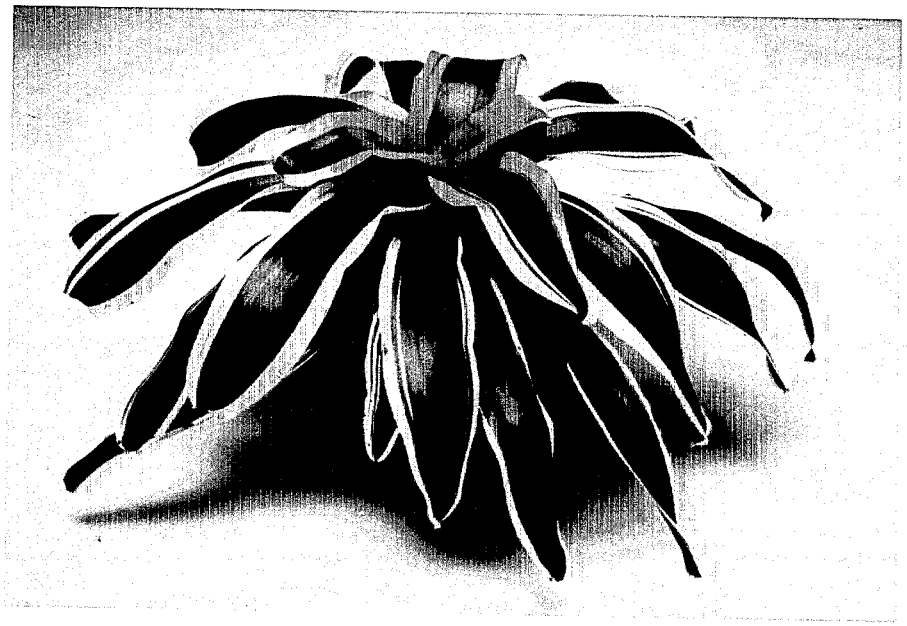

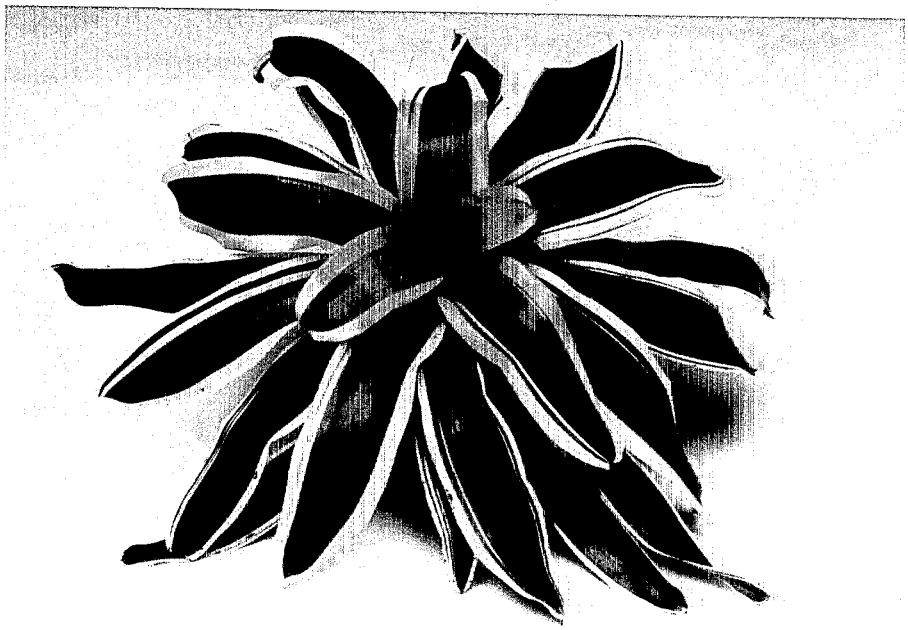

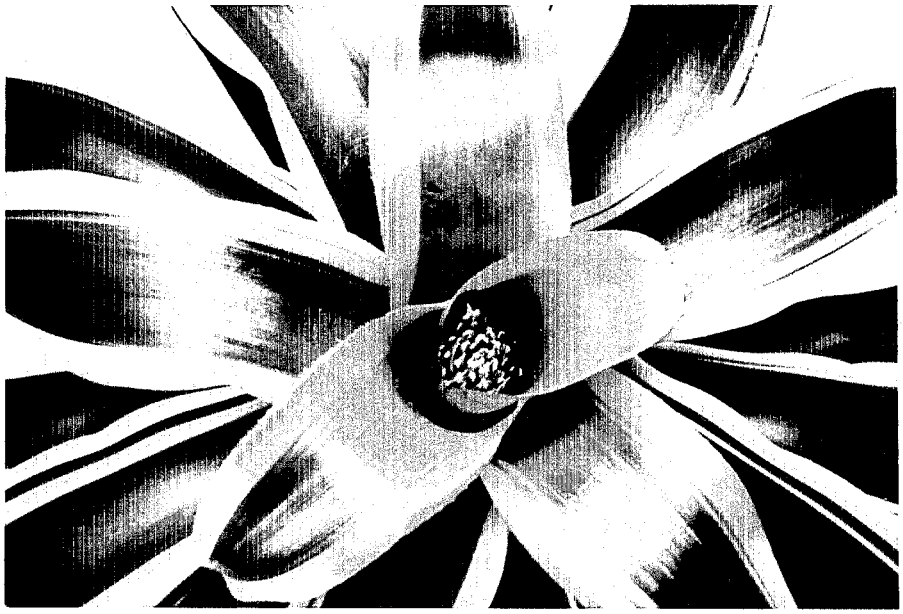

* * * * *